United States Patent [19]
King et al.

[11] Patent Number: 5,872,134
[45] Date of Patent: Feb. 16, 1999

[54] 5-HT4 RECEPTOR ANTAGONISTS

[75] Inventors: Francis David King; Laramie Mary Gaster, both of Bishop's Stortford; Keith Raymond Mulholland, Harlow, all of England

[73] Assignee: SmithKline Beecham p.l.c., Brentford, United Kingdom

[21] Appl. No.: 13,138

[22] Filed: Jan. 26, 1998

Related U.S. Application Data

[62] Division of Ser. No. 553,390, Nov. 22, 1995, Pat. No. 5,741,801.

[30] Foreign Application Priority Data

May 22, 1993 [GB] United Kingdom ................... 9310582

[51] Int. Cl.$^6$ ...................... A61K 31/445; A61K 31/395; A61K 31/425; A61K 31/42
[52] U.S. Cl. .......................... 514/323; 514/210; 514/373; 514/379; 514/403; 514/428
[58] Field of Search ................................. 514/323, 210, 514/373, 379, 403, 428

[56] References Cited

U.S. PATENT DOCUMENTS 5,741,801  4/1998  King et al. ............................. 514/323

Primary Examiner—Raymond J. Henley, III
Attorney, Agent, or Firm—Soma G. Simon; Charles M. Kinzig

[57] ABSTRACT

The use of a compound of formula (I) or a pharmaceutically acceptable salt thereof for the treatment of artrial arrhythmia, stroke or CNS disorders $$X-CO-CH_2-Z \quad (I)$$

wherein

X is a monocyclic or polycyclic aromatic group,

Z is of sub-formula (h), (j) or (k):

and wherein the remaining variables are as defined herein.

8 Claims, No Drawings

5-HT4 RECEPTOR ANTAGONISTS

This is a divisional of application Ser. No. 08/553,390, filed Nov. 22, 1995 now U.S. Pat. No. 5,741,801.

This invention relates to novel compounds having pharmacological activity, to a process for their preparation and to their use as pharmaceuticals.

European Journal of Pharmacology 146 (1988), 187–188, and Naunyn-Schmiedeberg's Arch. Pharmacol. (1989) 340:403–410, describe a non classical 5-hydroxytryptamine receptor, now designated the 5-HT$_4$ receptor, and that ICS 205–930, which is also a 5-HT$_3$ receptor antagonist, acts as an antagonist at this receptor.

WO 91/16045 (SmithKline and French Laboratories Limited) describes the use of cardiac 5-HT$_4$ receptor antagonists in the treatment of atrial arrhythmias and stroke.

EP-A-501322 (Glaxo Group Limited), WO 93/02677, WO 93/03725, WO 93/05038, WO 93/05040, WO 93/18036, PCT/EP93/03054, PCT/GB93/01895, PCT/GB93/02028, PCT/EP93/02808, PCT/EP93/02775, PCT/EP93/02809, PCT/GB93/02130, PCT/EP93/003054, PCT/GB94/000172 (SmithKline Beecham plc) describe compounds having 5-HT$_4$ receptor antagonist activity.

It has now been discovered that certain novel compounds also have 5-HT$_4$ receptor antagonist properties.

Accordingly, the present invention provides a compounds of formula (I) and pharmaceutically acceptable salts thereof, and the use of a compound of formula (I) or a pharmaceutically acceptable salt thereof:

X—CO—CH$_2$—Z    (I)

X is a monocyclic or polycyclic aromatic group, such as a group of formula (a), (b), (c), (d), (e), (f) or (g):

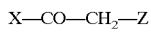
(a)

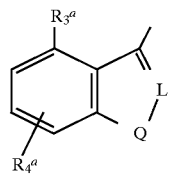
(b)

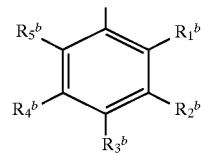
(c)

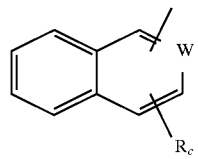
(d)

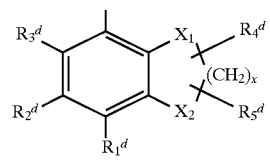
(e)

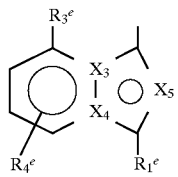
(e)

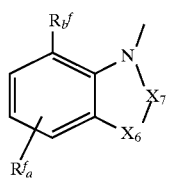
(f)

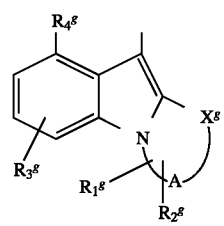
(g)

wherein
L is N or CR$_S$ wherein R$_S$ is hydrogen, C$_{1-6}$ alkoxy, halogen, C$_{1-4}$ alkyl or cyano;

Q is NR$_1{}^a$, CH$_2$, O or S;

W is CH or N;

X$_1$—(CH$_2$)$_x$—X$_2$ forms a 5–7 membered ring wherein X$_1$ is O or S; X$_2$ is O, S, —CH$_2{}^-$, NR or NRCO wherein R is hydrogen or C$_{1-6}$ alkyl; and x is 1, 2 or 3;

one of X$_3$ and X$_4$ is N and the other is C; and

X$_5$ is N or CR$^1$ wherein R$^1$ is hydrogen, C$_{1-6}$ alkoxy, halo, C$_{1-6}$ alkyl or cyano;

R$_1{}^a$ is hydrogen, C$_{1-10}$ alkyl, C$_{2-6}$ alkenyl, aralkyl, C$_{2-6}$ alkanoyl or C$_{2-6}$ alkanoyl C$_{1-3}$ alkyl;

R$_3{}^a$ is hydrogen, halo, C$_{1-6}$ alkyl, amino, nitro or C$_{1-6}$ alkoxy;

R$_4{}^a$ is hydrogen, halo, C$_{1-6}$ alkyl or C$_{1-6}$ alkoxy;

R$_1{}^b$ is C$_{1-6}$ alkoxy; and

R$_2{}^b$ is hydrogen, chloro or fluoro;

R$_3{}^b$ is hydrogen, C$_{1-6}$ alkyl, amino optionally substituted by a C$_{1-6}$ alkyl group, halo, hydroxy or C$_{1-6}$ alkoxy;

R$_4{}^b$ is hydrogen, halo, C$_{1-6}$ alkyl, C$_{1-6}$ alkoxy, nitro, amino or C$_{1-6}$ alkylthio; and R$_5{}^b$ is hydrogen, halo, C$_{1-6}$ alkyl, C$_{1-6}$ alkoxy or amino;

R$_c$ is hydrogen, C$_{1-6}$ alkoxy, halo or C$_{1-6}$ alkyl;

R$_1{}^d$ is hydrogen, amino, halo, C$_{1-6}$ alkyl, hydroxy or C$_{1-6}$ alkoxy;

R$_2{}^d$ is hydrogen, halo, C$_{1-6}$ alkyl, C$_{1-6}$ alkoxy, nitro, amino or C$_{1-6}$ alkylthio;

R$_3{}^d$ is hydrogen, halo, C$_{1-6}$ alkyl, C$_{1-6}$ alkoxy or amino;

R$_4{}^d$ and R$_5{}^d$ are independently hydrogen or C$_{1-6}$ alkyl;

R$_1{}^e$ is hydrogen, halogen, CF$_3$, C$_{1-6}$ alkyl, C$_{1-6}$ alkoxy, C$_{1-6}$ alkylthio, C$_{1-6}$ alkylsulphonyl, C$_{1-6}$ alkylsulphinyl, C$_{1-7}$ acyl, cyano, C$_{1-6}$ alkoxycarbonyl, C$_{1-7}$ acylamino, hydroxy, nitro or amino, aminocarbonyl, or aminosulphonyl, optionally N-substituted by one or two groups selected from C$_{1-6}$ alkyl, C$_{3-8}$ cycloalkyl, and C$_{3-8}$ cycloalkyl C$_{1-4}$ alkyl or disubstituted by C$_4$ or C$_5$ polymethylene; phenyl or phenyl $C_{1-4}$ alkyl group optionally substituted in the phenyl ring by one or two of halogen, $C_{1-6}$ alkoxy or $C_{1-6}$ alkyl groups;

$R_3^e$ is hydrogen, halo, $C_{1-6}$ alkyl, amino, nitro or $C_{1-6}$ alkyl;

$R_4^e$ is hydrogen, halo, $C_{1-6}$ alkyl or $C_{1-6}$ alkoxy;

$X_6$—$X_7$ is $NR_Z$—CO or $CR_1^f R_2^f$—$CR_3^f R_4^f$ where $R_Z$ and $R_1^f$ to $R_4^f$ are independently hydrogen or $C_{1-6}$ alkyl; and/or $R_1^f/R_2^f$ and $R_3^f/R_4^f$ together are a bond and/or $R_1^f/R_2^f/R_3^f/R_4^f$ are joined to form $C_{3-6}$ polymethylene;

$R_a^f$ is hydrogen, halo, $C_{1-6}$ alkyl, amino, nitro or $C_{1-6}$ alkyl;

$R_b^f$ is hydrogen, halo, $C_{1-6}$ alkyl or $C_{1-6}$ alkoxy;

$X^g$ is O, S, SO, $SO_2$, $CH_2$, CH, N or NR wherein R is hydrogen or $C_{1-6}$ alkyl;

A is a saturated or unsaturated polymethylene chain of 2–4 carbon atoms;

$R_1^g$ and $R_2^g$ are hydrogen or $C_{1-6}$ alkyl;

$R_3^g$ is hydrogen, halo, $C_{1-6}$ alkyl, amino, nitro or $C_{1-6}$ alkoxy;

$R_4^g$ is hydrogen, halo, $C_{1-6}$ alkyl or $C_{1-6}$ alkoxy;

Z is of sub-formula (h), (j) or (k):

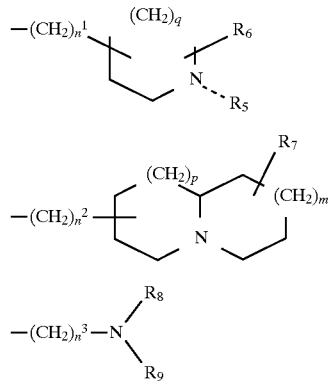

wherein $n^1$ is 1, 2, 3 or 4; $n^2$ is 0, 1, 2, 3 or 4; $n^3$ is 2, 3, 4 or 5; q is 0, 1, 2 or 3; p is 0, 1 or 2; m is 0, 1 or 2;

$R_5$ is hydrogen, $C_{1-12}$ alkyl, aralkyl or $R_5$ is $(CH_2)_z$-$R_{10}$ wherein z is 2 or 3 and $R_{10}$ is selected from cyano, hydroxyl, $C_{1-6}$ alkoxy, phenoxy, $C(O)C_{1-6}$ alkyl, $COC_6H_5$, —$CONR_{11}R_{12}$, $NR_{11}COR_{12}$, $SO_2NR_{11}R_{12}$ or $NR_{11}SO_2R_{12}$ wherein $R_{11}$ and $R_{12}$ are hydrogen or $C_{1-6}$ alkyl; or $R_5$ is straight or branched chain alkylene of chain length 1–6 carbon atoms terminally substituted by aryl, 3 to 8 membered cycloalkyl, 3 to 8 membered heterocyclyl, 5 or 6 membered monocyclic heteroaryl or 9 or 10 membered fused bicyclic heteroaryl linked through carbon, $C_{2-7}$ alkoxycarbonyl, or secondary or tertiary hydroxy substituted $C_{1-6}$ alkyl; and $R_6$, $R_7$ and $R_8$ are independently hydrogen or $C_{1-6}$ alkyl; and $R_9$ is hydrogen or $C_{1-10}$ alkyl;

having 5-$HT_4$ receptor antagonist activity.

Examples of alkyl or alkyl containing groups include $C_1$, $C_2$, $C_3$, $C_4$, $C_5$, $C_6$, $C_7$, $C_8$, $C_9$, $C_{10}$, $C_{11}$ or $C_{12}$ branched, straight chained or cyclic alkyl, as appropriate. $C_{1-4}$ alkyl groups include methyl, ethyl, n- and iso-propyl, n-, iso-, sec- and tert-butyl. Cyclic alkyl includes cyclopropyl, cyclobutyl, cyclopentyl, cyclohexyl, cycloheptyl and cyclooctyl optionally substituted by one of more alkyl groups of up to 4 carbon atoms.

Aryl includes phenyl and naphthyl optionally substituted by one or more substituents selected from halo, $C_{1-6}$ alkyl and $C_{1-6}$ alkoxy.

Values for monocyclic heteroaryl include pyridyl, pyrimidyl, pyrazinyl, pyrryl, imidazolyl, thienyl, furanyl, oxazole or thiazole (all possible isomers). Bicyclic heteroaryl include benzofuranyl, benzothiophenyl, indolyl and indazolyl, quinolyl and isoquinolyl (all possible isomers).

Values for 3 to 8 membered heterocyclyl, include cyclic polymethylene interrupted by one or two of N, O or S, linked through C or N, for example N-linked piperidinyl or pyrrolidinyl.

Halo includes fluoro, chloro, bromo and iodo, preferably chloro.

L in formula (a) is favourably C—H, C—$CH_3$, C—Cl or C—$OCH_3$.

Q in formula (a) is favourably $NR_1^a$.

$R_1^a$ is preferably hydrogen or a methyl or ethyl group.

$R_1^b$ is preferably methoxy.

$R_3^b$ is preferably amino.

$R_4^b$ is preferably halo.

$R_5^b$ is preferably hydrogen.

A substituent when halo is selected from fluoro, chloro, bromo and iodo. $R_4^a$ when halo is preferably iodo.

Suitable examples of the $X_1$—$(CH_2)_x$—$X_2$ moiety include O—$(CH_2)_2$—O, O—$(CH_2)_3$—O, O—$CH_2$—O, O—$(CH_2)_2$—NR, O—$(CH_2)_2$—S or O—$CH_2$—CONR, wherein any of the methylene linkages are optionally mono- or di- substituted by $C_{1-6}$ alkyl groups, such as methyl. Preferably $X_1$—$(CH_2)_2$—$X_2$ is O—$(CH_2)_2$—O.

Further suitable examples of $X_1$—$(CH_2)_x$—$X_2$ include O—$(CH_2)_2$—$CH_2$, O—$(CH_2)_3$—$CH_2$, O—$CH_2$—$CH_2$, or corresponding values wherein $X_1$=$X_2$=$CH_2$, wherein any of the methylene linkages are optionally mono- or di-substituted by $C_{1-6}$ alkyl groups, such as methyl. Preferably such $X_1$—$(CH_2)_2$—$X_2$ is O—$(CH_2)_2$—$CH_2$.

$R_1^d$ is preferably hydrogen or amino.

$R_2^d$ is preferably hydrogen or halo.

$R_3^d$ is preferably hydrogen or halo.

$R_4^d$ and $R_5^d$ are often hydrogen. When $R_4^d$ or $R_5^d$ is $C_{1-6}$ alkyl, it is often methyl.

$R_1^e$ is preferably $CF_3$ or an ethyl group.

$X_5$ is preferably N, C—H or C—$OCH_3$;

$R_3^e$ is preferably hydrogen.

$R_4^e$ is preferably hydrogen or halo, such as iodo.

Suitable examples of $X_6$-$X_7$ when $CR_1^f R_2^f$-$CR_3^f R_4^f$ include $CH_2$—$CH_2$ and CH=CH. $X_6$-$X_7$ is preferably $NR_Z$—CO, however, such as NH—CO or NEt-CO.

$R_a^f$ is preferably hydrogen.

$R_b^f$ is preferably hydrogen or halo, such as iodo.

Values for A include —$CH_2$—$(CH_2)_r$—$CH_2$— wherein r is 0, 1 or 2; —$CH_2$—CH=CH—; —$C(CH_3)$=CH— or when $X^g$ is CH or N, A may be —$(CH_2)_2$—CH= or —CH=CH—CH=. Other examples of A are as described in the aforementioned patent publications.

$R_1^g$ and $R_2^g$ are often hydrogen or $R_1^g$ and $R_2^g$ are gem-dimethyl.

r is often 1.

$R_3^g$ is preferably hydrogen.

$R_4^g$ is preferably hydrogen or halo, such as fluoro.

Other suitable values of X are as described in PCT/GB93/020208, PCT/EP93/02808, PCT/EP93/02775, PCT/EP93/02809, PCT/GB93/02130, PCT/GB94/00172 (all in the name of SmithKline Beecham plc).

When Z is of sub-formula (h), $n^1$ is preferably 2, 3 or 4 when the azacycle is attached at the nitrogen atom and n1 is preferably 1 when the azacycle is attached at a carbon atom, such as the 4-position when q is 2.

When Z is of sub-formula (j), $n^2$ is preferably such that the number of carbon atoms between the ester or amide linkage is from 2 to 4 carbon atoms.

Suitable values for p and m include p=m=1; p=0, m=1, p=1, m=2 p=2, m=1.

When Z is of sub-formula (k), $n^3$ is preferably 2, 3 or 4.

$R_8$ and $R_9$ are preferably both alkyl, especially one of $R_8$ and $R_9$ is $C_4$ larger alkyl.

Specific values of Z of particular interest are as follows:

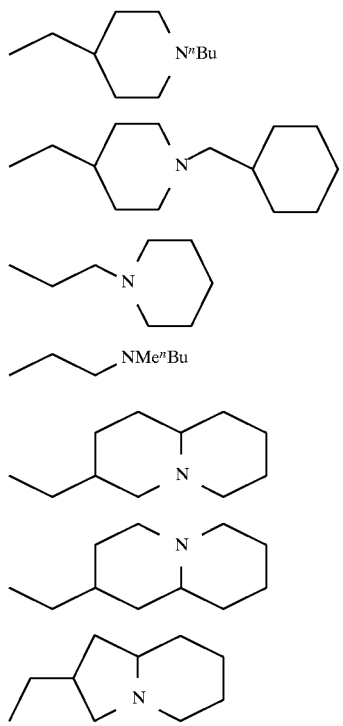

The invention also provides novel compounds within formula (I) with side chains (i), (ii), (iii), (iv), (v), (vi) or (vii). In a further aspect, the piperidine ring in (i), (ii) or (iii) may be replaced by pyrrolidinyl or azetidinyl, and/or the N-substituent in (i) or (ii) may be replaced by $C_3$ or larger alkyl or optionally substituted benzyl.

In an alternative aspect, the N-substituent in formula (i) or (ii) may be replaced by $(CH_2)_nR_4$ as defined in formula (I) of EPA 501322 and in relation to the specific examples of EP-A-501322, or it may be replaced by a substituent as as defined in formula (I) and in relation to the specific examples of in PCT/EP93/03054 (SmithKline Beecham plc).

The pharmaceutically acceptable salts of the compounds of the formula (I) include acid addition salts with conventional acids such as hydrochloric, hydrobromic, boric, phosphoric, sulphuric acids and pharmaceutically acceptable organic acids such as acetic, tartaric, maleic, citric, succinic, benzoic, ascorbic, methanesulphonic, a-keto glutaric, a-glycerophosphoric, and glucose-1-phosphoric acids.

Examples of pharmaceutically acceptable salts include quaternary derivatives of the compounds of formula (I) such as the compounds quaternised by compounds $R_X$-T wherein $R_X$ is $C_{1-6}$ alkyl, phenyl-$C_{1-6}$ alkyl or $C_{5-7}$ cycloalkyl, and T is a radical corresponding to an anion of an acid. Suitable examples of $R_X$ include methyl, ethyl and n- and iso-propyl; and benzyl and phenethyl. Suitable examples of T include halide such as chloride, bromide and iodide.

Examples of pharmaceutically acceptable salts also include internal salts such as N-oxides.

The compounds of the formula (I), their pharmaceutically acceptable salts, (including quaternary derivatives and N-oxides) may also form pharmaceutically acceptable solvates, such as hydrates, which are included wherever a compound of formula (I) or a salt thereof is herein referred to.

The compounds of formula (I) may be prepared by conventional methods for forming ketones, such as those described in EP-A-242973 (Glaxo Group Limited) and EP-A-387431 (Beecham Group plc).

Reference is made to the aforemetioned patent publications in the name of Beecham Group plc in respect of intermediates containing X and Z moieties.

The compounds of the present invention are 5-$HT_4$ receptor antagonists and it is thus believed may generally be used in the treatment or prophylaxis of gastrointestinal disorders, cardiovascular disorders and CNS disorders.

They are of potential interest in the treatment of irritable bowel syndrome (IBS), in particular the diarrhoea aspects of IBS, i.e., these compounds block the ability of 5-HT to stimulate gut motility via activation of enteric neurones. In animal models of IBS, this can be conveniently measured as a reduction of the rate of defaecation. They are also of potential use in the treatment of urinary incontinence which is often associated with IBS.

They may also be of potential use in other gastrointestinal disorders, such as those associated with upper gut motility, and as antiemetics. In particular, they are of potential use in the treatment of the nausea and gastric symptoms of gastrooesophageal reflux disease and dyspepsia. Antiemetic activity is determined in known animal models of cytotoxicagent/radiation induced emesis.

Specific cardiac 5-$HT_4$ receptor antagonists which prevent atrial fibrillation and other atrial arrhythmias associated with 5-HT, would also be expected to reduce occurrence of stroke (see A. J. Kaumann 1990, Naumyn-Schmiedeberg's Arch. Pharmacol. 342, 619–622, for appropriate animal test method).

Anxiolytic activity is likely to be effected via the hippocampus (Dumuis et al 1988, Mol Pharmacol., 34, 880–887). Activity can be demonstrated in standard animal models, the social interaction test and the X-maze test.

Migraine sufferers often undergo situations of anxiety and emotional stress that precede the appearance of headache (Sachs, 1985, Migraine, Pan Books, London). It has also been observed that during and within 48 hours of a migraine attack, cyclic AMP levels are considerably increased in the cerebrospinal fluid (Welch et al., 1976, Headache 16, 160–167). It is believed that a migraine, including the prodomal phase and the associated increased levels of cyclic AMP are related to stimulation of 5-$HT_4$ receptors, and hence that administration of a 5-$HT_4$ antagonist is of potential benefit in relieving a migraine attack.

Other CNS disorders of interest include schizophrenia, Parkinson's disease and Huntingdon's chorea.

The invention also provides a pharmaceutical composition comprising a compound of formula (I), or a pharmaceutically acceptable salt thereof, and a pharmaceutically acceptable carrier.

Such compositions are prepared by admixture and are usually adapted for enteral such as oral, nasal or rectal, or parenteral administration, and as such may be in the form of tablets, capsules, oral liquid preparations, powders, granules, lozenges, reconstitutable powders, nasal sprays, suppositories, injectable and infusable solutions or suspensions. Orally administrable compositions are preferred, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art, for example with an enteric coating.

Suitable fillers for use include cellulose, mannitol, lactose and other similar agents. Suitable disintegrants include starch, polyvinylpolypyrrolidone and starch derivatives such as sodium starch glycollate. Suitable lubricants include, for example, magnesium stearate.

Suitable pharmaceutically acceptable wetting agents include sodium lauryl sulphate. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral liquid preparations are usually in the form of aqueous or oily suspensions, solutions, emulsions, syrups, or elixirs or are presented as a dry product for reconstitution with water or other suitable vehicle before use. Such liquid preparations may contain conventional additives such as suspending agents, emulsifying agents, non-aqueous vehicles (which may include edible oils), preservatives, and flavouring or colouring agents.

The oral compositions may be prepared by conventional methods of blending, filling or tabletting. Repeated blending operations may be used to distribute the active agent throughout those compositions employing large quantities of fillers. Such operations are, of course, conventional in the art.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure of ethylene oxide before suspending in the sterile vehicle. Advantageously, a surfactant or wetting agent is included in the composition to facilitate uniform distribution of the compound of the invention.

The invention further provides a method of treatment or prophylaxis of irritable bowel syndrome, dyspepsia, atrial arrhythmias and stroke, anxiety and/or migraine in mammals, such as humans, which comprises the administration of an effective amount of a compound of the formula (I) or a pharmaceutically acceptable salt thereof.

An amount effective to treat the disorders hereinbefore described depends on the relative efficacies of the compounds of the invention, the nature and severity of the disorder being treated and the weight of the mammal. However, a unit dose for a 70 kg adult will normally contain 0.05 to 1000 mg for example 0.5 to 500 mg, of the compound of the invention. Unit doses may be administered once or more than once a day, for example, 2, 3 or 4 times a day, more usually 1 to 3 times a day, that is in the range of approximately 0.0001 to 50 mg/kg/day, more usually 0.0002 to 25 mg/kg/day.

No adverse toxicological effects are indicated within the aforementioned dosage ranges.

The invention also provides a compound of formula (I) or a pharmaceutically acceptable salt thereof for use as an active therapeutic substance, in particular for use in the treatment of irritable bowel syndrome, gastro-oesophageal reflux disease, dyspepsia, atrial arrhythmias and stroke, anxiety and/or migraine.

The following Examples illustrates the preparation of compounds of formula (I), and the following Descriptions relate to the preparation of intermediates.

A preferred compound corresponds to any example, but wherein there is an amino substituent in the 4-position and a chloro substituent in the 5-position of the benzoic acid nucleus depicted in formula (I).

EXAMPLE 1

[X=a), L=CH, Q=NCH$_3$, R$_3^a$ and R$_4^a$=H, Z=(i)]

a) 1-(1-Methyl-1H-indol-3-yl)-3-(4-pyridyl)-propan-1-one

The product from Description 1, (0.190 g, 0.540 mmol) was dissolved in trifluoroacetic acid (7 ml), and heated to reflux with stirring. After 4h, the reaction mixture was allowed to cool, was diluted with water and treated with aq. potassium carbonate until basic. The aqueous suspension was then extracted with CHCl$_3$ (2X). The combined organic layers were then dried (Na$_2$SO$_4$), and evaporated under reduced pressure to give an orange solid, which was dried in vacuo (0.101 g). The solid was then dissolved in EtOH (15 ml), treated with 10% PdC, and hydrogenated at atmospheric pressure. After 16 h, the reaction mixture was filtered through kieselguhr, evaporated under reduced pressure, and dried in vacuo to give the title compound as a colourless oil (0.100 g, 69%).

$^1$H NMR (250MHz, CDCl$_3$), δ 8.50 (d, 2H), 8.35 (m, 1H), 7.70 (s, 1H), 7.40–(m, 5H), 3.84 (s, 3H), 3.15 (m, 4H).

b) 1-(1-Methyl-1H-indol-3-yl)-3-(1-butylpiperidin-4-yl) propan-1-one

The product from a) above (0.100 g, 0.379 mmol) was dissolved in acetone (4 ml), and treated with 1-bromobutane (0.122 ml, 1.137 mmol) and the mixture was heated to reflux with stirring. After 3 h, a further amount of 1-bromobutane (0.122 ml, 1.137 mmol) was added and reflux continued overnight. More 1-bromobutane was then added (0.244 ml, 2.274 mmol), and reflux continued for a further 8 h. The reaction mixture was then evaporated under reduced pressure and the residue dissolved in ethanol (10 ml) and acetic acid (0.5 ml). Platinum (IV) oxide (0.03 g) was then added and the mixture hydrogenated at atmospheric pressure. After 16 h, the reaction mixture was filtered through kieselguhr and the filtrate evaporated under reduced pressure and dried in vacuo. The product was then purified by silica-gel chromatography (CH$_2$Cl$_2$/10% MeOH as eluant) to give the title compound as a pale yellow oil (0.052 g, 43%) which was converted to its oxalate salt m.pt 124°–126° C. (oxalate salt)

$^1$H NMR (200MHz, CDCl$_3$)-free base-δ 8.38 (m, 1H), 7.80 (s, 1H), 7.32 (m, 3H), 3.90 (s, 3H), 3.20 (d, 2H), 2.90

(t, 2H), 2.58 (t, 2H), 2.28 (t, 2H), 1.90–1.50 (m, 8H), 1.35 (m, 3H), 0.95 (t, 3H).

EXAMPLE 2

[X=(g), $X^g$=O, A=(CH$_2$)$_3$, $R_1^g$, $R_2^g$, $R_3^g$, $R_4^g$=H; Z=(i)]

a) 1-(3,4-Dihydro-2H-[1,3]oxazino[3,2a]indol-10-yl)-3-hydroxy-3-(4-pyridyl)propan-1-one 1.6M n-Butyllithium (1.67 ml, 2.67 mmol) was added to dry THF (12 ml), containing diisopropylamine (0.374 ml, 2.67 mmol) under argon at 0° C. with stirring. After 15 minutes, the mixture was cooled to −78° C., and the product from Description 2 (0.420 g, 2.43 mmol) in dry THF (8 ml) was added slowly. The resulting mixture was then left at −78° C. for 1h, before pyridine-4-carboxaldehyde (0.232 ml, 2.43 mmol) was added. After a further 1 h, at −78° C., the reaction mixture was allowed to warm to room temperature, whereupon the reaction mixture was quenched with aq. ammonium chloride. The reaction mixture was then partitioned between ethyl acetate and water. The aqueous layer was then extracted with ethyl acetate (1X), and the combined organic layers were dried (Na$_2$SO$_4$), and evaporated under reduced pressure to give a pale brown solid, which was purified by silica-gel chromatography (CH$_2$Cl$_2$/5% MeOH as eluant) to give the title compound as an off white solid (0.246 g, 31%).

$^1$H NMR (200MHz, CDCl$_3$) δ 8.54 (d, 2H), 8.27 (d, 1H), 7.40–7.00 (m, 5H), 5.30 (dd, 1H), 4.88 (s, 1H), 4.50 (t, 2H), 4.10 (t, 2H), 3.30 (dd, 1H), 3.05 (dd, 1H), 2.33 (m, 2H).

b) E-1-(3,4-Dihydro-2H-[1,3]oxazino[3,2a]indol-3-yl)-3(4-pyridyl)-prop-2-en-1-one The product from a) (0.220 g, 6.83 mmol) was dissolved in trifluoroacetic acid (20 ml), and heated to reflux with stirring. After 4h, the reaction mixture was allowed to cool and was evaporated under reduced pressure. The residue was then treated with aq. sodium bicarbonate and the resultant yellow suspension was extracted with CHCl$_3$ (3X). The combined organic layers were then dried (Na$_2$SO$_4$), and evaporated under reduced pressure to give a yellow solid. The solid was purified by silica-gel chromatography (CH$_2$Cl$_2$/5% MeOH as eluant) to give the title compound as a yellow solid (0.190 g, 92%).

$^1$H NMR (200MHz, CDCl$_3$) δ 8.60 (d, 2H), 8.45 (d, 1H), 7.80 (d, 1H), 7.62 (d, 1H), 7.40 (d, 2H), 7.35–7.00 (m, 3H), 4.60 (t, 2H), 4.03 (t, 2H), 2.48–2.30 (m, 2H).

c) 1-(3,4-Dihydro-2H-[1,3]oxazino[3,2a]indol-10-yl)-3(4-pyridyl)propan-1-one

The product from b) (0.190 g, 0.625 mmol) was dissolved in ethanol (40 ml) and hydrogenated at atmospheric pressure in the presence of 10% PdC (0.05 g). After 17 h, the reaction mixture was filtered through kieselguhr, and the filtrate evaporated under reduced pressure and dried in vacuo to give a colourless oil, which was purified by silica-gel chromatography (CH$_2$Cl$_2$/5% MeOH as eluant) to give the title compound as a pale yellow solid (0.130 g, 68%).

$^1$H NMR (200MHz, CDCl$_3$) δ 8.48 (d, 2H), 8.32 (d, 1H), 7.32–7.05 (m, 5H), 4.50 (t, 2H), 4.08 (t, 2H), 3.20–2.95 (m, 4H), 2.35 (m, 2H).

d) 1-(3,4-Dihydro-2H-[1,3]oxazino[3,2a]indol-10-yl)-3(1-butyl-4-piperidinyl)propan-1-one The product from c) (0.120 g, 0.392 mmol) was dissolved in acetone (4 ml), and treated with 1-bromobutane (0.127 ml, 1.18 mmol) and heated to reflux with stirring. After 2h, and 5h, further amounts of 1-bromobutane were added, (0.127 ml, 1.18 mmol) and (0.254 ml, 2.36 mmol) respectively. Reflux was continued for a further 15 h. The reaction mixture was then evaporated under reduced pressure, and dried in vacuo. The off white solid obtained was then redissolved in ethanol (20 ml) containing acetic acid (0.5 ml); platinum (IV) oxide (0.03 g) was then added and the mixture was hydrogenated at atmospheric pressure. After 24 h, the reaction mixture was filtered through kieselguhr, and the filtrate evaporated under reduced pressure and dried in vacuo. The reaction mixture was then purified by silica-gel chromatography (CH$_2$Cl$_2$/10% MeOH as eluant) to give the title compound as an off white solid (0.053 g, 37%), which was converted to its oxalate salt. m.pt 156°–159° C. (oxalate salt).

$^1$H NMR (200MHz, CDCl$_3$)-free base-δ 8.32 (d, 1H), 7.30–7.05 (m, 3H), 4.55 (t, 2H), 4.12 (t, 2H), 3.20 (d, 2H), 2.88 (t, 2H), 2.60 (t, 2H), 2.45–2.18 (m, 4H), 1.95–1.50 (m, 9H), 1.35 (m, 2H), 0.97 (t, 3H).

Description 1

(Intermediate for Example 1)

a) 3-Acetyl-1-methyl-1H-indole

3-Acetyl-1H-indole (4.00 g, 0.025 mol) was dissolved in dry THF (100 ml), and treated with 80% sodium hydride (0.794 g, 0.0263 mol) with stirring under Ar. After 0.5 h, methyl iodide (2.36 ml, 0.038 mol) was added. After 20 h, the reaction mixture was evaporated under reduced pressure and the residue partitioned between ethyl acetate and water. The organic layer was then dried (Na$_2$SO$_4$), and evaporated under reduced pressure to give the title compound as a pale brown oil which crystallised on standing (4.20 g, 97%).

$^1$H NMR (250MHz, CDCl$_3$), δ 8.40 (m, 1H), 7.70 (s, 1H), 7.30 (m, 3H), 3.85 (s, 3H), 2.52 (s, 3H).

b) 1-(1-Methyl-1H-indol-3-yl)-3-(4-pyridyl)-3-trimethylsilyloxypropan-1-one 1.6M n-Butyllithium (1.19 ml, 1.90 mmol) was added to dry THF (10 ml) containing diisopropylamine (0.266 ml, 1.90 mmol) under Ar at 0° C. After 15 mins, the mixture was cooled to −78° C., and 3-acetyl-1-methyl-1H-indole (0.300 g, 1.73 mmol) in dry THF (5 ml) was added slowly. The resulting mixture was left at −78° C. for 1 h, before pyridine-4-carboxaldehyde (0.165 ml, 1.73 mmol) was added. The reaction mixture was then left at −78° C. for 1 h, before being allowed to warm to 0° C., whereupon chlorotrimethylsilane (0.439 ml, 3.46 mmol) was added. The mixture was then allowed to warm to room temp and stirred for 1 h, before being evaporated under reduced pressure and partitioned between dichloromethane and water. The organic layer was then dried (Na$_2$SO$_4$) and evaporated under reduced pressure to give a pale yellow solid which was purified by silica-gel chromatography (EtOAc as eluant) to give the title compound as a yellow solid (0.300 g, 51%).

$^1$H NMR (270MHz, CDCl$_3$) δ 8.54 (d, 2H), 8.40 (m, 1H), 7.63 (s, 1H), 7.38 (d, 2H), 7.30 (m, 3H), 5.45 (dd, 1H), 3.80 (s, 3H), 3.30 (dd, 1H), 2.92 (dd, 1H), 0.0 (s, 9H).

Description 2

(Intermediate for Example 2)

a) N-Methoxy-N-methyl-(1H-indol-3-yl)-carboxamide

Indole-3-carboxylic acid (2.50 g, 0.0155 mol) was suspended in dichloromethane (60 ml) and treated with oxalyl chloride (1.62 ml, 0.0186 mol), followed by a drop of dry DMF. The reaction mixture was then stirred at room temperature overnight, before being evaporated under reduced pressure and dried in vacuo. The product was then redissolved in dichloromethane (50 ml) and added slowly to a solution of N,O-dimethylhydroxylamine hydrochloride (1.59 g, 0.0163 mol) in dichloromethane (50 ml) containing triethylamine (4.53 ml, 0.0326 mol) under argon. The resultant mixture was then stirred at room temperature for 2h, before being washed with water, followed by aq. NaHCO$_3$. The organic layer was then dried (Na$_2$SO$_4$), evaporated under reduced pressure and dried in vacuo to yield the title compound as white solid (2.46 g, 78%).

$^1$H NMR (200MHz, CDCl$_3$) δ 9.00 (s, 1H), 8.40 (m, 1H), 7.90 (d, 1H), 7.40 (m, 1H), 7.25 (m, 2H), 3.70 (s, 3H), 3.40 (s, 3H).

b) N-Methoxy-N-Methyl-(3,4-dihydro-2H-[1,3]oxazino[3,2a]indol-10-yl]carboxamide

The product from a) (2.42 g, 0.0119 mol) was suspended in chloroform (95 ml), with stirring, and treated with triethylamine (1.65 ml, 0.0119 mol) and 3-bromopropanol (2.15 ml, 0.0238 mol), followed by N-chlorosuccinimide (1.85 g, 0.0139 mol). The mixture was then stirred at room temperature for 1.5 h. 1M HCl in diethyl ether (0.333 ml, 0.333 mmol), was then added. After 5 minutes, and 10 minutes, further quantities of 1M HCl (0.333 ml) were added. Upon addition of the last quantity of HCl, the temperature was observed to rise to 34° C. After a further 0.5 h, the reaction mixture was washed with 10% Na$_2$CO$_3$. The organic layer was then dried (Na$_2$SO$_4$), evaporated under reduced pressure and dried in vacuo, before being redissolved in acetone (70 ml) and treated with anhydrous K$_2$CO$_3$ (3.07 g, 0.0222 mol) with stirring. The reaction mixture was then stirred overnight, filtered, and the filtrate evaporated under reduced pressure to give a brown oil, which was dried in vacuo, and then purified by silica-gel chromatography (EtOAc as eluant) to give the title compound as a colourless oil which crystallised on standing (2.60 g, 84%).

$^1$H NMR (200MHz, CDCl$_3$) δ 7.75 (m, 1H), 7.25–7.10 (m, 3H), 4.50 (t, 2H), 4.12 (t, 2H), 3.70 (s, 3H), 3.32 (s, 3H), 2.35 (m, 2H).

c) 10-Acetyl-3,4-dihydro-2H-[1,3]oxazino[3,2a]indole

The product from b) (0.99 g, 3.81 mmol) was dissolved in dry THF, cooled to 0° C., and treated with 3.0M methylmagnesium bromide in diethyl ether (1.41 ml, 4.24 mmol) under argon, with stirring. After 20 minutes at 0° C., the reaction mixture was allowed to warm to room temperature, and after 2 h, a further quantity of 3.0M methylmagnesium bromide (1.41 ml, 4.24 mmol) was added. The reaction mixture was then stirred for a further 2 h, before aq. ammonium chloride was added. The reaction mixture was then partitioned between EtOAc and water. The aqueous layer was then extracted with EtOAc, and the combined organic layers were dried (Na$_2$SO$_4$) and evaporated under reduced pressure to give a red solid. Recrystalisation of the solid from EtOAc gave the title compound as a pale pink solid (0.275 g, 34%). A further quantity of the title compound was obtained by silica-gel chromatography (pentane:EtOAc, 1:2 as eluant) of the filtrate from the recrystallisation, to give the title compound as a cream solid (0.152 g, 18%).

$^1$H NMR (250MHz, CDCl$_3$) δ 8.32 (d, 1H), 7.30–7.00 (m, 3H), 4.52 (t, 2H), 4.05 (t, 2H), 2.50 (s, 3H), 2.35 (m, 2H).

5-HT$_4$ RECEPTOR ANTAGONIST ACTIVITY

1) Guinea Pig Colon

Male guinea-pigs, weighing 250–400 g are used. Longitudinal muscle-myenteric plexus preparations, approximately 3 cm long, are obtained from the distal colon region. These are suspended under a 0.5 g load in isolated tissue baths containing Krebs solution bubbled with 5% CO$_2$ in O$_2$ and maintained at 37° C. In all experiments, the Krebs solution also contains methiothepin 10-7M and granisetron 10-6M to block effects at 5-HT$_1$, 5-HT$_2$ and 5-HT$_3$ receptors.

After construction of a simple concentration-response curve with 5-HT, using 30 s contact times and a 15 min dosing cycle, a concentration of 5-HT is selected so as to obtain a contraction of the muscle approximately 40–70% maximum(10-9M approx). The tissue is then alternately dosed every 15 min with this concentration of 5-HT and then with an approximately equi-effective concentration of the nicotine receptor stimulant, dimethylphenylpiperazinium (DMPP). After obtaining consistent responses to both 5-HT and DMPP, increasing concentrations of a putative 5-HT$_4$ receptor antagonist are then added to the bathing solution. The effects of this compound are then determined as a percentage reduction of the contractions evoked by 5-HT or by DMPP. From this data, pIC$_{50}$ values are determined, being defined as the –log concentration of antagonist which reduces the contraction by 50%. A compound which reduces the response to 5-HT but not to DMPP is believed to act as a 5-HT$_4$ receptor antagonist.

The compound of Example 1 had a pIC$_{50}$ of 6.8.

What is claimed is:

1. A method of treating atrial arrhythmia or stroke which comprises administering a compound of formula (I) or a pharmaceutically acceptable salt thereof:

X—CO—CH$_2$—Z    (I)

wherein

X is of formula (a):

wherein

L is N or CR$_S$ wherein R$_S$ is hydrogen, C$_{1-6}$ alkoxy, halogen, C$_{1-4}$ alkyl or cyano;

Q is NR$_1^a$, CH$_2$, O or S;

R$_1^a$ is hydrogen, C$_{1-10}$ alkyl, C$_{2-6}$ alkenyl, aralkyl, C$_{2-6}$ alkanoyl or C$_{2-6}$ alkanoyl C$_{1-3}$ alkyl;

R$_3^a$ is hydrogen, halo, C$_{1-6}$ alkyl, amino, nitro or C$_{1-6}$ alkoxy;

R$_4^a$ is hydrogen, halo, C$_{1-6}$ alkyl or C$_{1-6}$ alkoxy;

Z is of sub-formula (h), (j), or (k):

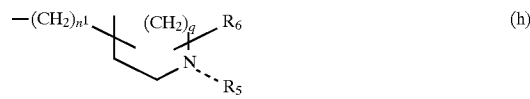

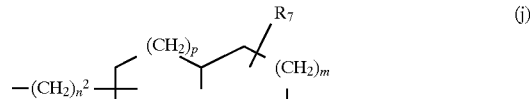

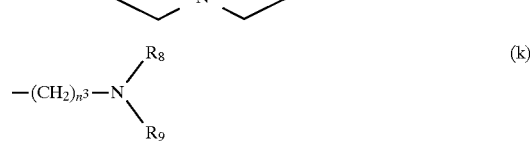

wherein n$^1$ is 1, 2, 3 or 4; n$^2$ is 0, 1, 2, 3 or 4; n$^3$ is 2, 3, 4 or 5; q is 0, 1, 2 or 3; p is 0, 1 or 2; m is 0, 1 or 2;

R$_5$ is hydrogen, C$_{1-12}$ alkyl, aralkyl or R$_5$ is (CH$_2$)$_z$-R$_{10}$ wherein z is 2 or 3 and R$_{10}$ is selected from cyano, hydroxyl, C$_{1-6}$ alkoxy, phenoxy, C(O)C$_{1-6}$ alkyl, COC$_6$H$_5$, —CONR$_{11}$R$_{12}$, NR$_{11}$COR$_{12}$, SO$_2$NR$_{11}$R$_{12}$ or NR$_{11}$SO$_2$R$_{12}$ wherein R$_{11}$ and R$_{12}$ are hydrogen or C$_{1-6}$ alkyl; or R$_5$ is straight or branched chain alkylene of chain length 1–6 carbon atoms terminally substituted by aryl, 3 to 8 membered cycloalkyl, 3 to 8 membered heterocyclyl, 5 or 6 membered monocyclic heteroaryl or 9 or 10 membered fused bicyclic heteroaryl linked through carbon, C$_{2-7}$ alkoxycarbonyl, or secondary or tertiary hydroxy substituted C$_{1-6}$ alkyl; and R$_6$, R$_7$ and R$_8$ are independently hydrogen or C$_{1-6}$ alkyl; and R$_9$ is hydrogen or C$_{1-10}$ alkyl.

2. A method according to claim 1 wherein:

L is C—H, C—CH$_3$, C—Cl or C—OCH$_3$;

Q is NR$_1^a$; and

R$_1^a$ is hydrogen, methyl or ethyl.

3. A method according to claim 1 wherein Z is a group (h) in which n$^1$ is 1 and the azacycle is attached at a 4-position carbon atom when q is 2, and Z is 4-piperidinylmethyl and 4-pyrrolidinylmethyl, N-substituted by R$_a$ as defined in claim 1.

4. A method according to claim 3 wherein the compound is 1-(1-Methyl-1H-indol-3-yl)-3-(1-butylpiperidin-4-yl) propan-1-one.

5. A method of treating a CNS disorder selected from the group consisting of migraine, schizophrenia, Parkinson's disease, Huntingdon's chorea and anxiety which comprises administering a compound of formula (I) or a pharmaceutically acceptable salt thereof:

(I)

wherein

X is of formula (a):

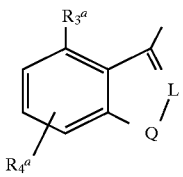

(a)

wherein

L is N or CR$_S$ wherein R$_S$ is hydrogen, C$_{1-6}$ alkoxy, halogen, C$_{1-4}$ alkyl or cyano;

Q is NR$_1^a$, CH$_2$, O or S;

R$_1^a$ is hydrogen, C$_{1-10}$ alkyl, C$_{2-6}$ alkenyl, aralkyl, C$_{2-6}$ alkanoyl or C$_{2-6}$ alkanoyl C$_{1-3}$ alkyl;

R$_3^a$ is hydrogen, halo, C$_{1-6}$ alkyl, amino, nitro or C$_{1-6}$ alkoxy;

R$_4^a$ is hydrogen, halo, C$_{1-6}$ alkyl or C$_{1-6}$ alkoxy;

Z is of sub-formula (h), (j) or (k):

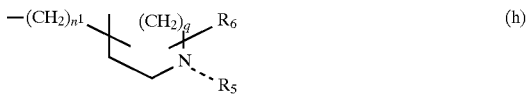

(h)

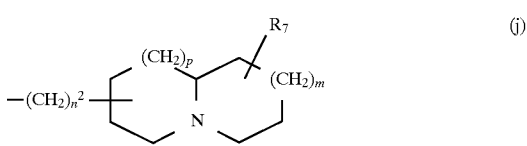

(j)

(k)

wherein n$^1$ is 1, 2, 3 or 4; n$^2$ is 0, 1, 2, 3 or 4; n$^3$ is 2, 3, 4 or 5;

q is 0, 1, 2 or 3; p is 0, 1 or 2; m is 0, 1 or 2;

R$_5$ is hydrogen, C$_{1-12}$ alkyl, aralkyl or R$_5$ is (CH$_2$)$_Z$-R$_{10}$ wherein z is 2 or 3 and R$_{10}$ is selected from cyano, hydroxyl, C$_{1-6}$ alkoxy, phenoxy, C(O)C$_{1-6}$ alkyl, COC$_6$H$_5$, —CONR$_{11}$R$_{12}$, NR$_{11}$COR$_{12}$, SO$_2$NR$_{11}$R$_{12}$ or NR$_{11}$SO$_2$R$_{12}$ wherein R$_{11}$ and R$_{12}$ are hydrogen or C$_{1-6}$ alkyl; or R$_5$ is straight or branched chain alkylene of chain length 1–6 carbon atoms terminally substituted by aryl, 3 to 8 membered cycloalkyl, 3 to 8 membered heterocyclyl, 5 or 6 membered monocyclic heteroaryl or 9 or 10 membered fused bicyclic heteroaryl linked through carbon, C$_{2-7}$ alkoxycarbonyl, or secondary or tertiary hydroxy substituted C$_{1-6}$ alkyl; and R$_6$, R$_7$ and R$_8$ are independently hydrogen or C$_{1-6}$ alkyl; and R$_9$ is hydrogen or C$_{1-10}$ alkyl.

6. A method according to claim 5 wherein:

L is C—H, C—CH$_3$, C—Cl or C—OCH$_3$;

Q is NR$_1^a$; and

R$_1^a$ is hydrogen, methyl or ethyl.

7. A method according to claims 5 wherein Z is a group (h) in which n$^1$ is 1 and the azacycle is attached at a 4-position carbon atom when q is 2, and Z is 4-piperidinylmethyl and 4-pyrrolidinylmethyl, N-substituted by R$_a$ as defined in claim 1.

8. A method according to claim 7 wherein the compound is 1-(1-Methyl-1H-indol-3-yl)-3-(1-butylpiperidin-4-yl) propan-1-one.

* * * * *

UNITED STATES PATENT AND TRADEMARK OFFICE
CERTIFICATE OF CORRECTION

PATENT NO. : 5,872,134
DATED : February 16, 1999
INVENTOR(S) : Francis David King; Laramie Mary Gaster; Keith Raymond Mulholland It is certified that error appears in the above-identified patent and that said Letters Patent is hereby corrected as shown below:

Title page,
ABSTRACT,
Claim 1 and Claim 5, the structure of sub-formula (h) is incorrect. In these three places, the correct structure of sub-formula (h) should be:

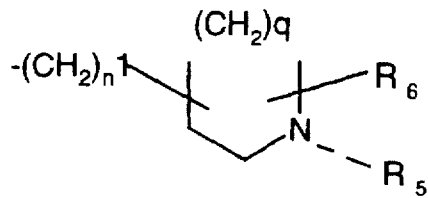

(h)

Signed and Sealed this

Twelfth Day of March, 2002

Attest:

JAMES E. ROGAN
Attesting Officer    Director of the United States Patent and Trademark Office